(12) United States Patent
Smithers et al.

(10) Patent No.: US 8,287,475 B2
(45) Date of Patent: Oct. 16, 2012

(54) APPARATUS AND METHOD FOR APPLYING AN ELECTROSTATIC FIELD TO A WOUND OR SCAR TO PROMOTE HEALING THEREOF

(75) Inventors: Mark W. Smithers, Framingham, MA (US); Frank S. Silveira, Wilmington, MA (US); David Jacofsky, Peoria, AZ (US); Alan A. Waldman, Oceanside, NY (US)

(73) Assignee: Technology Capital Investors, LLC, Phoenix, AZ (US)

( * ) Notice: Subject to any disclaimer, the term of this patent is extended or adjusted under 35 U.S.C. 154(b) by 754 days.

(21) Appl. No.: 12/002,428

(22) Filed: Dec. 17, 2007

(65) Prior Publication Data
US 2008/0275374 A1    Nov. 6, 2008

(51) Int. Cl.
*A61F 13/00*    (2006.01)
*A61N 1/00*    (2006.01)

(52) U.S. Cl. ............ 602/2; 602/41; 607/2; 607/50
(58) Field of Classification Search ........... 607/2, 50, 607/148, 149, 152; 600/9, 15; 602/2, 41–43, 602/48, 54
See application file for complete search history.

(56) References Cited

U.S. PATENT DOCUMENTS

| | | | |
|---|---|---|---|
| 6,861,570 B1 * | 3/2005 | Flick | 602/41 |
| 6,907,294 B2 * | 6/2005 | Andino et al. | 607/46 |
| 7,457,667 B2 | 11/2008 | Skiba | |
| 2003/0023270 A1 * | 1/2003 | Danz et al. | 607/2 |
| 2003/0216783 A1 * | 11/2003 | Lehtoluoto | 607/2 |
| 2004/0068296 A1 * | 4/2004 | Palti | 607/2 |
| 2009/0062723 A1 | 3/2009 | Skiba | |

* cited by examiner

*Primary Examiner* — Patricia Bianco
*Assistant Examiner* — Keri J Nelson
(74) *Attorney, Agent, or Firm* — Allen R. Kipnes, Esq.

(57) ABSTRACT

Apparatus in the form of a bandage for generating an electrostatic field which when placed in proximity to a wound or scar induces polarization therein to facilitate the healing process. Methods of treating wounds and scars particularly in humans utilizing the bandage is also disclosed.

24 Claims, 5 Drawing Sheets

APPARATUS AND METHOD FOR APPLYING AN ELECTROSTATIC FIELD TO A WOUND OR SCAR TO PROMOTE HEALING THEREOF

FIELD OF THE INVENTION

The present invention is generally directed to an apparatus and method for generating an electrostatic field and for directing the electrostatic field toward a wound or scar to promote healing of wounds and/or scars and to prevent scar formation in warm blooded animals including humans. The apparatus may be in the form of a bandage. The electrostatic field induces a charge in the wound or scar to facilitate healing of the wound, prevention or reduction of scar formation, or reduction of the adverse appearance of existing scars. No applied current is passed directly into the tissues of the patient, thus making the device inherently safe to use.

BACKGROUND OF THE INVENTION

Excessive scaring resulting from the healing of wounds can present a significant aesthetic and functional problem for patients after surgery or traumatic injury to the skin. Excessive scars are generally classified as hypertrophic scars or keloids. While these scars differ in appearance, they are the result of similar processes whereby skin and connective tissue cells deposit more tissue than is necessary to repair the wound. The deposition of excess tissue may continue for months and even years after the initial skin trauma and can in extreme cases, adversely affect the range of motion of joints. These scars are problematic because they can be painful, generate unpleasant itching or burning sensations, may be unsightly such as by differing in color from surrounding tissue, and may limit joint mobility when they occur in the skin around a joint. The strength of skin affected by scar formation may also be reduced. Skin lacking normal strength is susceptible to re-laceration of the tissue and thus further scarring. While there are topical creams, bandages, injections, and surgeries that may bring some reduction in the appearance of these scars, there is no reliable therapy for the prevention of scar formation or treatment for existing scars currently available. Therefore, it is desirable to have a mode of therapy to prevent scar formation and to reliably reduce the appearance and functional impact of severe scars including hypertrophic and keloid scars.

One approach taken by the prior art to treat wounds and/or scars is to pass an applied current (i.e alternative or direct current) into the body where the wound or scar forms part of the primary electrical circuit. However, such systems are disadvantageous because: 1—applying an applied current to the body may pose a risk to patients with cardiac assistive devices such as pacemakers and defibrillators; 2—applying an applied current to the body can impact medical instruments used to monitor patients under medical supervision, such as, EKG and EEG; 3—applying an applied current may damage (burn) tissues of the body if arching occurs or if the applied current exceeds safe levels; 4—applying an applied current in close proximity to a nerve can cause unwanted muscle activity and/or pain; and 5—the maximum applied current that can be applied safely to avoid the aforementioned complications has not been adequately studied.

One effort to minimize the deleterious effects of an applied current is the use of static electricity. Bernard Hirshowitz et al. *Plastic Reconstr. Surg., Vol.* 101 (5) April 1998 disclose a bandage for treatment of hypertrophic and keloid scars using silicone cushions which, upon actuation by exerting pressure with the fingers, generates negative static electricity in which "the interaction between the negatively charged ions of the cushion and the ionic charges of the tissue fluids may be the critical factor in achieving hypertrophic and keloid scar involution". Nonetheless, the reference system employs an applied current which remains problematic.

There have been efforts to treat wounds and scars without using an applied current. One treatment for scar tissue that has received attention in the medical literature without using an applied current makes use of silicone occlusive bandages. Alexandrina S. Saulis (*Aesthetic Surg. J.* Vol. 22, Issue 2, pp. 147-153 (2002) disclose a reduction in the severity of scars when silicone occlusive bandages are used in animal models during the healing process.

For wound healing, it was observed from U.S. Pat. No. 4,142,521 that weak electrostatic fields provided by electret-type devices within a wafer thin disposable bandage could enhance the healing process. Electret materials, as described in the reference, are permanently polarized pieces of dielectric materials which may be made by subjecting a dielectric material to a strong electric potential difference. Elisa Burgess et al., *Plastic Reconstr. Surg.*, Vol. 102(7) December 1998 disclose that positively charged cross-linked diethylaminoethyl dextran beads could significantly enhance the tensile properties of healing wounds. The electrostatic charge contained in the active materials used in the prior art serves to polarize the soft tissue of the wound or scar and it is this polarization which appears to contribute to wound and scar healing.

The systems employed in the prior art described above which have avoided the use of an applied current have limitations because the electrostatic charge associated with these systems and particularly electret materials are of limited intensity and it is believed that a greater intensity of the electrostatic field is needed to achieve adequate wound and/or scar healing.

Accordingly, Applicants have developed a device in the form of a bandage capable of generating an electrostatic field at the site of a wound and/or scar in which the intensity of the electrostatic field can be varied according to the particular wound and/or scar to be treated. The intensity of the electrostatic field can exceed that associated with electret materials and therefore obtain a beneficial healing effect without the use of an applied current. The present device also provides the ability to alter the polarity of the induced electrostatic field which may likewise positively impact wound and/or scar treatment.

SUMMARY OF THE INVENTION

The present invention is directed to a bandage for the treatment of wounds and/or scars and for the prevention or reduction of scar tissue that typically results from healing wounds which generates an electrostatic field of sufficient intensity to promote healing. The bandage employs an electrostatic field generating assembly which includes the ability to control and vary the intensity of the electrostatic field so that the bandage may be adapted to effectively treat a variety of wounds and scars and affect healing thereof. The present invention does not make use of an applied current that is passed into the wound or any other part of the patient's body and thus the patient's body is not part of the primary circuit established by the present invention. Instead, the electrostatic field generated by the present invention induces a change of polarity in at least a portion of the wound or scar which is believed to facilitate the healing process. The present invention therefore mitigates the concerns of using applied current by not passing current into the tissues while still creating polarization in the skin and underlying tissues.

Electrostatic fields when applied to wounds and scars pose significantly less risk to the patient than applied currents because an electric current is not applied directly to the skin. Rather, the electrostatic field generating device of the present invention develops the charge within an insulative material and therefore there is no direct current contact with the skin of the patient. As a result, the patient's body is not part of the primary circuit.

In one aspect of the invention there is provided a bandage for generating an electrostatic field and for inducing a charge in a wound or scar as a result of said generated electrostatic field to promote healing thereof comprising:

an electrostatic field generating assembly for generating an electrostatic field and for delivering the electrostatic field to said wound or scar, including electrostatic field control means for controlling the intensity of the electrostatic field to achieve a level of intensity sufficient to induce polarization in said wound or scar necessary to promote healing thereof;

In another aspect of the invention, there is provided a method of treating wounds and/or scars utilizing the bandage of the present invention. The present invention provides particular application to the treatment of wounds and scars in humans.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

Disclosed herein is a device in the form of a bandage applied to the skin of a patient in proximity to a wound or scar. The device generates an electrostatic field at the site of the wound or scar using electronic components housed within the bandage to generate the desired field. As used herein the term "wound" includes: surgical incisions, cuts, punctures, tears, sores, ulcers, blisters, burns, and other breaches of the skin. A scar is intended to include hypertrophic scars, keloids, or any healed wound tissue that is unsightly or of concern to the afflicted individual or their care provider.

Unlike some prior art systems that rely on alternating currents and direct currents (i.e. applied current) to treat wounds and scars, the present invention avoids the use of such currents. The bandage includes an electrostatic field generating assembly which provides the means to generate and direct an electrostatic field in proximity to the wound or scar and also the means to control the intensity of the electrostatic field in a manner sufficient to initiate and maintain the healing process.

Figure 1:
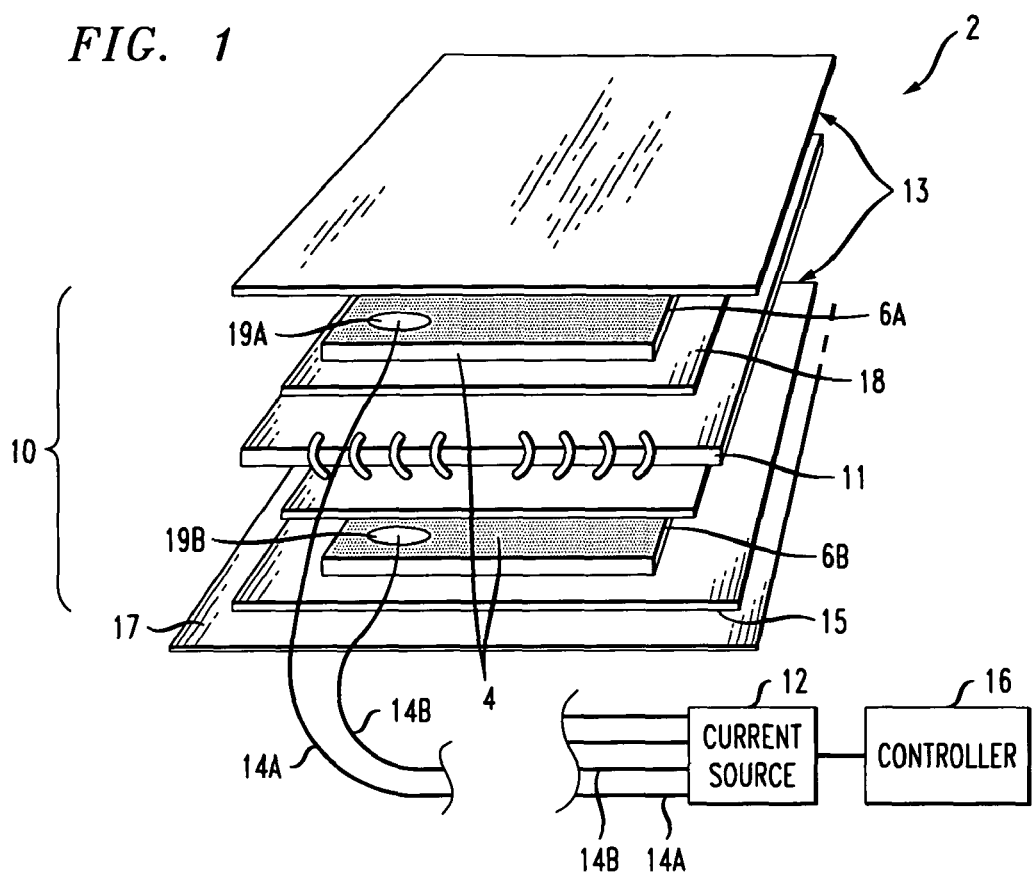
FIG. 1 is a perspective view of a first embodiment of a bandage of the present invention including an electrostatic field generating assembly.
Figure 2A:
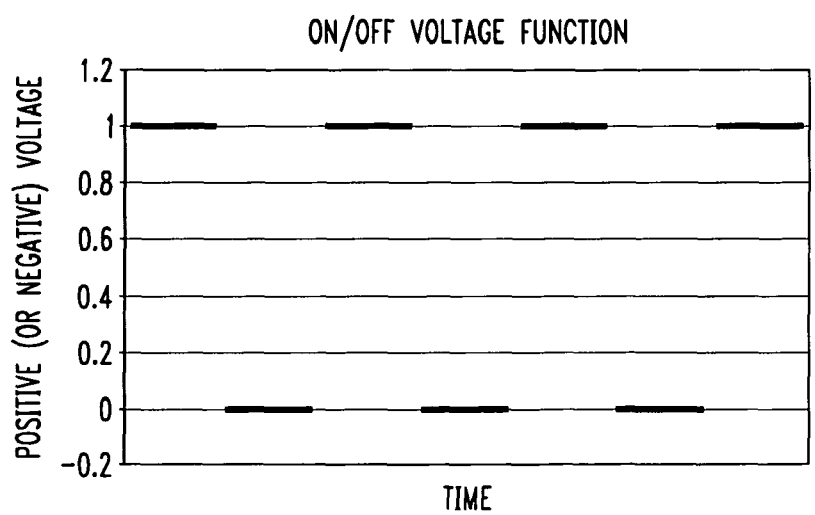
FIGS. 2A-2D are graphs showing wave functions generated by a controller employed as part of the electrostatic field generating assembly.
Figure 2B:
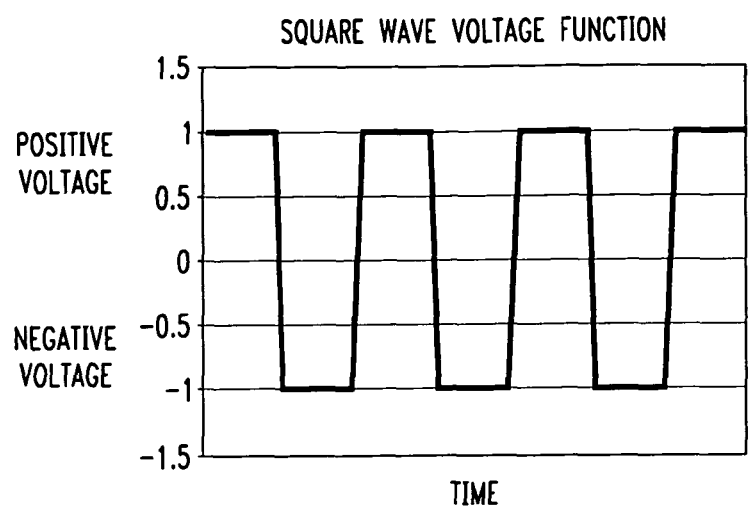
Figure 2C:
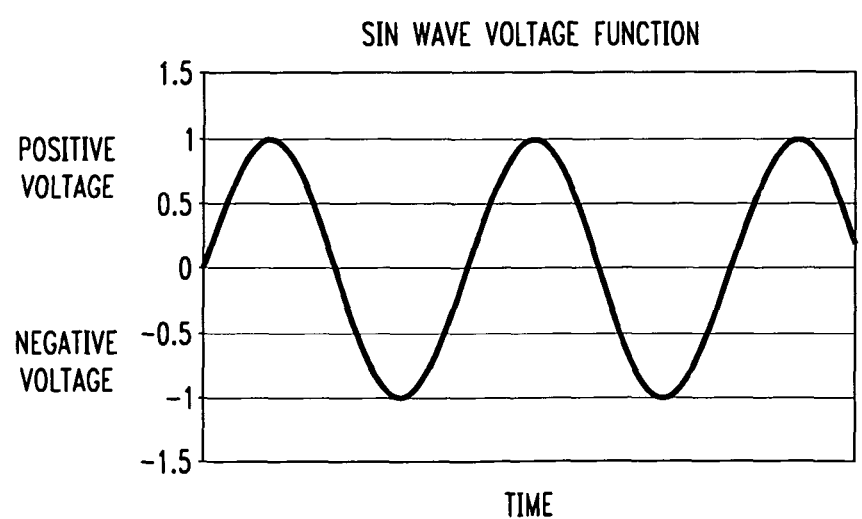
Figure 2D:
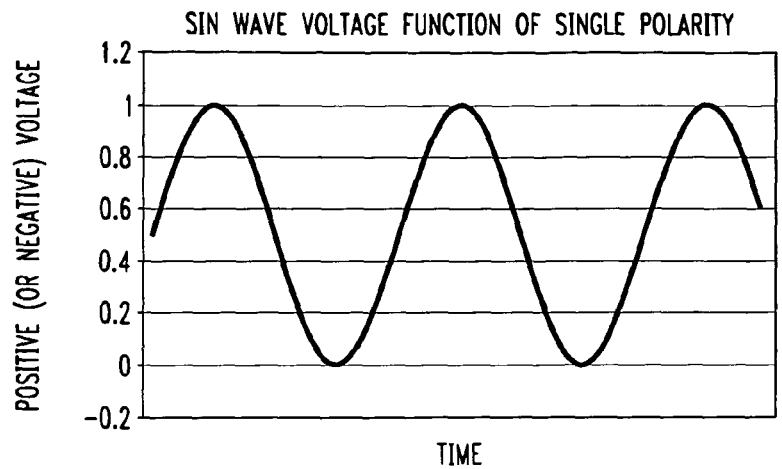

In one embodiment of the invention as shown in FIG. 1, a bandage 2 includes a parallel plate assembly 4 including conductive plates 6A and 6B comprised of a conductive material such as copper, aluminum or a conductive ink imprinted on a substrate. The plates are encased within a non-conductive dielectric assembly 10 which may be in the form of an envelope or comprised of separate dielectric sheets of material joined together about the plates such as by an adhesive or through heat sealing. In the embodiment specifically shown in FIG. 1, the plates 6A, 6B are separated from each other by a dielectric layer 11 made of a suitable dielectric material such as a silicone based material which is joined by an adhesive (not shown) to outer insulative layers 13 such as Mylar so as to encase the plates 6A, 6B within the insulative dielectric assembly 10. The plates 6A, 6B may be secured within the dielectric assembly 10 by adhering the plates to an additional and optional adhesive layer 18. Mylar has a dielectric breakdown strength of 5 kilovolts per mil. The thickness of the Mylar is typically 0.003 to 0.005 inch. A 3 mil Mylar layer could therefore use as much as 5 kilovolts. The silicone dielectric layer has a typical dielectric strength of 1000 v/mil. A 0.010 inch layer could use approximately 3 kilovolts as the applied voltage. Generally the thickness of the dielectric layer can be in the range of 0.003 to 0.1 inch.

The plates 6A and 6B are connected to an electric current source 12 through positive and negative terminals. In this arrangement, the plates 6A and 6B essentially act as a capacitor, with one plate 6A or 6B becoming positive and the other plate 6A or 6B becoming negative since no current can flow between the plates. In the preferred embodiment, the plates are made of thin copper foil and the dielectric material is a flexible sheet made of a silicone based material. This embodiment takes the currently available materials used in silicone occlusive bandages and adds additional field strength and field control to facilitate wound healing and scar treatment.

Figure 8:
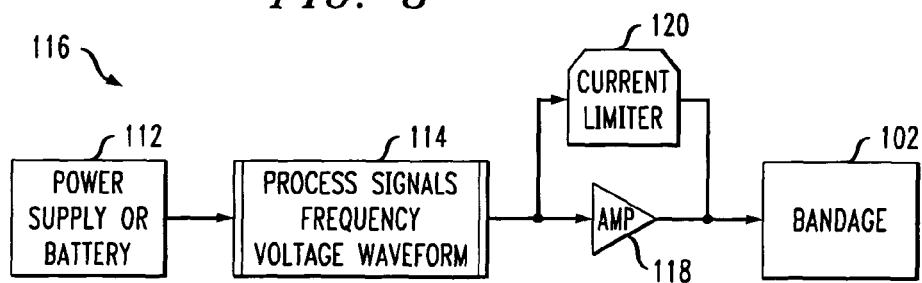
FIG. 8 is a block diagram of the controller employed as part of the electrostatic field generating assembly.

A pair of lead wires 14A, 14B are attached to the plates 6A, 6B via contact areas 19A, 19B respectively and run to the current source 12 which includes a controller 16. It will be noted that additional lead wires exit from the current source 12 to indicate that more than one bandage 2 can be connected to a single current source 12. The controller 16 such as shown in FIG. 8 generates both AC and DC current in a range of voltages which can be determined and selected by the user according to need and in accordance with the nature of the wound or scar including the type and size of the wound and scar. Thus, a myriad of combinations of polarities and wave forms can be generated. The controller 16 is preferably battery powered but can be plugged into standard outlets for recharging or running directly off of the power grid.

The structure of the controller 16 is shown in FIG. 8. The controller 116 is connected to a current source 112 enabling the controller to be powered by either internally or externally contained batteries or from a power supply which receives power from a main line. A signal generator 114 produces waveforms of various shapes (e.g. sinusoidal, triangular, square, etc.) at a range of frequencies and voltages which also can includes a DC output signal.

An amplifier 118 is provided to amplify the low output signal (voltage) from the signal generator to produce amplified signal which is sent to the plate assembly contained within the bandage 102.

There is also provided a current limiter 120 which limits the peak currents that can pass through the system as a safety measure. In the event of damage to the leads or the bandage, peak currents are limited to prevent the wearer or handler of the bandage from adverse exposure. The standard peak current limit for medical devices is typically in the range of 300 uA-500 uA.

As shown in FIGS. 2A-2D, the controller may change the voltage from positive to negative in an on/off or continuous modes through the selection of DC current or may adjust the voltage through the selection of alternating current from positive to negative in a continuous sine wave or may adjust the voltage of a single polarity (e.g. positive) in a continuous sine wave. It should be noted that the voltage values depicted in FIGS. 2A-2D are for illustrative purposes only and are not necessarily voltage values that would be employed in a commercial embodiment of the device.

Thus, a way of affecting the induced field by modifying and controlling the intensity and shape of the induced electrostatic field is to cycle the voltage applied to plurality of the plates. This can be achieved by applying a time varying voltage (sinusoidal or other periodic output, or for periods of on and off cycling or reversal of polarity in a direct current application).

The parallel plate assembly 4 may be designed to achieve a desired electrostatic field both with respect to shape and polarity. By way of example and as shown in FIG. 1, the plates 6A, 6B can be positioned such that both plates are parallel to the surface being treated and the plates are stacked upon each other with an insulative (dielectric) envelope surrounding the plates. In this configuration, one of the plates will be charged either positively or negatively. The plate closer to the surface being treated (e.g. the positive plate) will induce a charge of opposite polarity (e.g. negative charge) in the treatment area which is believed to facilitate the healing process. The bandage 2 shown in FIG. 1 may be secured to the skin of the patient 17 in proximity to the wound by conventional means including the use of conventional adhesive strips (not shown) attached to the parallel plate assembly 4 or by providing an adhesive layer (not shown) on the bottom side of the lower insulative material 13 lying closest to the skin when the bandage is in an operative position about the wound.

The bandage 2 described above generates an electrostatic field in which the intensity can be selected and maintained at a level sufficient to assist the healing process for wound and scars. The electrostatic field induces polarization of the wound or scar tissues without having such tissues as part of the primary circuit.

Control of the electrostatic field including depth of penetration of the field into the wound or scar and the intensity of the field is dependent on the voltage applied to the bandage, the type and thickness of the insulative material surrounding the conductive plates, the insulative value of the insulative material (i.e. the degree to which the insulative material prevents the flow of current) and the thickness or depth of the wound or scar. Thus, for a given thickness and type of insulative material surrounding the plates increasing the voltage will increase the intensity of the electrostatic field applied to the wound or scar.

The current required to keep the bandage at the desired voltage must be less than the maximum limits for leakage. This is needed in the event the bandage is damaged. The current that could be passed to the user would be limited by the current limiter (see FIG. 8) to a maximum of typically 300 to 500 uA.

Figure 3:
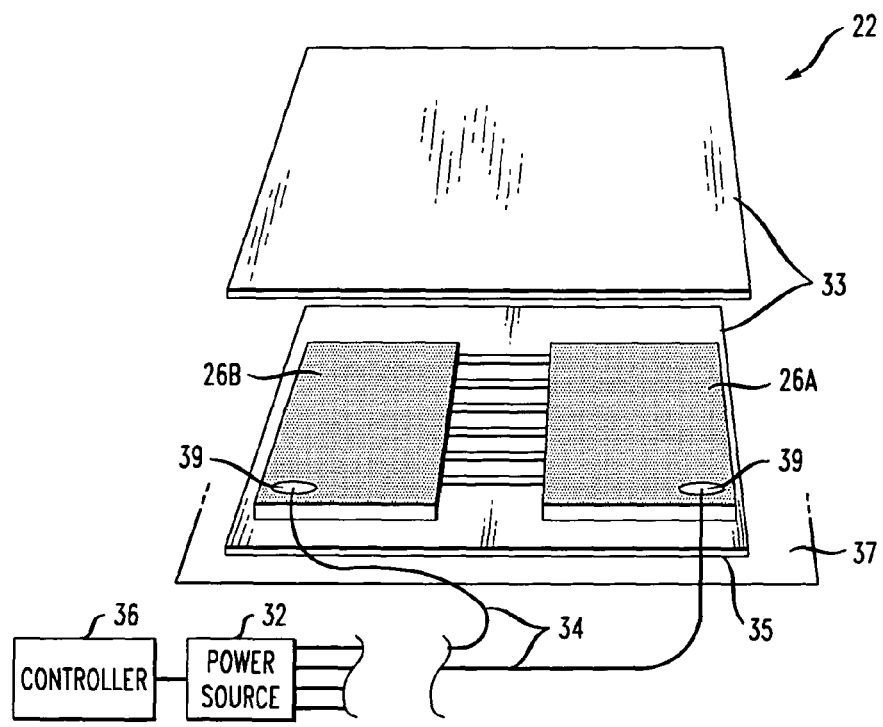
FIG. 3 is a perspective view of a second embodiment of a bandage of the present invention.

In a second embodiment of the invention as shown in FIG. 3, a bandage 22 includes a parallel plate assembly 24 comprised of parallel plates 26A, 26B made of an electrically conductive material, covered by a dielectric assembly 32 encompassing the parallel plates comprised of insulative sheets 33 such as silicone based materials having an optional adhesive backing layer 35 for securing the bandage to the skin 37. The plates are connected to a power source 32 as similarly described in FIG. 1 which includes a controller 36, through lead wires 34 and contacts 39. As described in connection with the embodiment of FIG. 1, multiple bandages may be operated by a single current source.

The parallel plates are parallel to each other in the same plane, thus creating two parallel charged plates equidistant from the surface being treated. In this arrangement, the region of skin beneath each plate will have an induced charge opposite to that of the overlying plate. If the plates are placed at the margins of a wound or scar, each side of the treatment zone will be exposed to an equal and opposite charge. If the plates are moved off center, such that one plate overlies the wound or scar and the other overlies a non-affected area of the skin, the entire wound or scar will have an induced field of single polarity. This produces the same effect as the embodiment in FIG. 1, however with a different electrode configuration.

Figure 4:
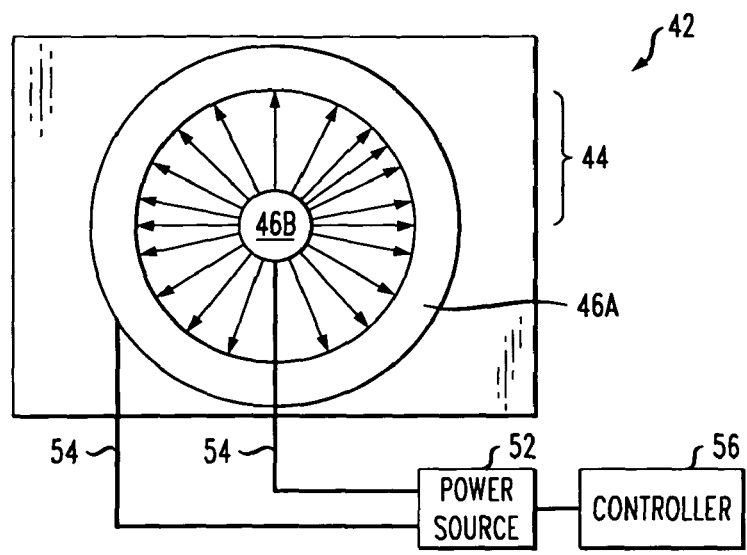
FIG. 4 is a perspective view of a third embodiment of a bandage of the present invention.

A third embodiment of the bandage of the present invention is shown in FIG. 4. There is shown a bandage 42 comprised of a parallel plate assembly 44 in which parallel plates 46A, 46B are arranged in a concentric circular pattern. The plates are connected to a power source 52 through lead wires 54 and control of the intensity and polarity of the electrostatic field is maintained through controller 56 as previously described. In this arrangement the desired polarity of treatment is centered over the wound or scar being treated and may approximate the shape of certain wounds more effectively than the parallel plate arrangements shown in FIGS. 1 and 3.

Figure 5:
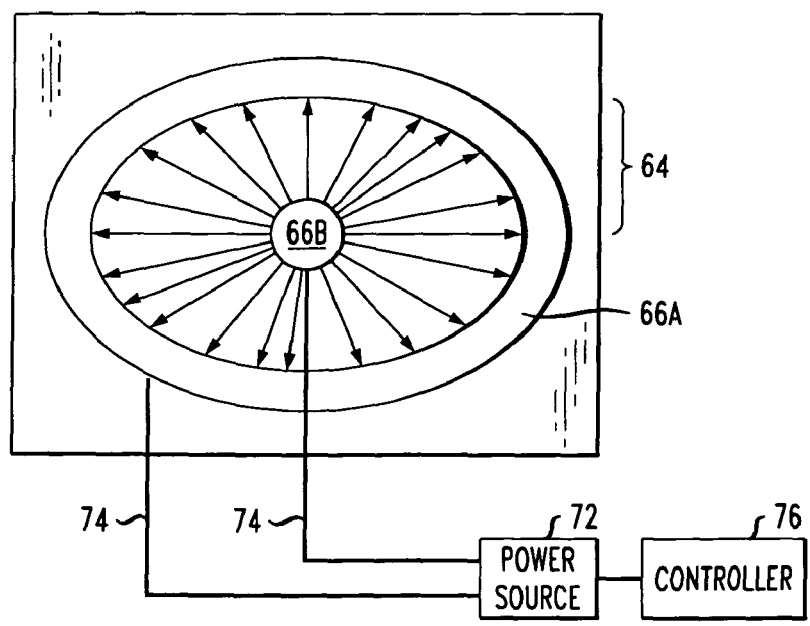
FIG. 5 is a perspective view of a fourth embodiment of a bandage of the present invention.

A fourth embodiment of the invention is shown in FIG. 5 in which the parallel plate assembly represented by numeral 64 comprises two concentric oval plates 66A and 66B connected to a power source 72 via leads 74. The intensity and polarity of the electrostatic field is controlled by a controller 76 as previously described.

Figure 6:
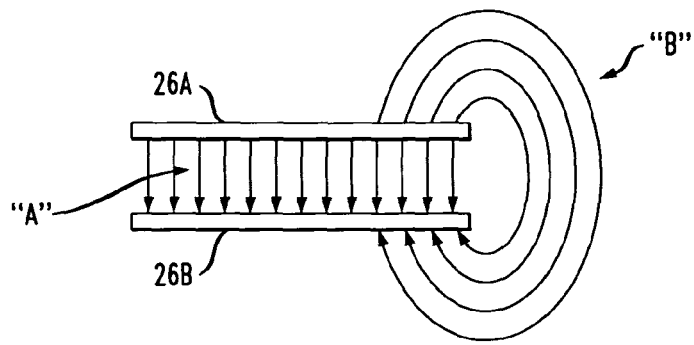
FIG. 6 is a diagrammatic view of an electrostatic field produced from the bandage of the present invention shown in FIG. 1.

The generation of an electrostatic field by the bandages of the present invention and the ability to control the intensity and shape of the electrostatic field is discussed below. The embodiment of the bandage of the present invention shown in FIG. 1 has two spaced apart plates of a conductive material encompassed by an insulated material to form essentially a capacitor. As shown in FIG. 6, two parallel plates thus having a construction similar to FIG. 1 generate an electrostatic field in which the field lines are illustrated when a voltage is applied to the plates. The gap between the plates is filled with a dielectric material. The dielectric material is a non-conducting material and polarizes under the influence of the applied voltage. As a solid material, it keeps the plates from contacting each other thus preventing a short circuit. The field between the plates is the primary field designated by "A" while a secondary field designated by "B" exists at the end of the plates in the form of concentric field lines. The intensity of the field may be increased by increasing the voltage applied to the parallel plates within a range of 0.1 mv or less up to and exceeding 2 kilovolts (kv). The shape of the field may be altered by, for example, altering the distance between the parallel plates, by changing the shape of the plates (e.g. from square to circular), by changing the size of the plates, and by changing the orientation of the plates (e.g. from a stacked to parallel arrangement).

The apparatus of the present invention employs a dielectric material covering the outside surfaces of the upper and lower parallel plates of sufficient thickness to prevent current flow between the plates and into the patient's tissue. As a result, an abundance of positive or negative charges are generated at the surface of the dielectric covering. This in turn presents a substantially positive (or negative) area adjacent to the outside of the dielectric covering. If the voltage applied is that of direct current, the device acts substantially like an electret (see FIGS. 2A and 2B). Electrons are not free to move into/out of the device and do not conduct current into the body subject, of course to the limits of the dielectric material in preventing current flow. Depending upon the plate geometry (i.e. size and shape), alternating current or pulse input voltage may be used to move currents induced in the body as a result of moving ions near the surface of the substrate (e.g. wound) or away from the insulated plate adjacent to the body.

The controller employed in the electrostatic field generating assembly is capable of generating wave functions of varying frequency and also capable of generating constant direct current so that there is no variation in the intensity or polarity of the electrostatic field.

The attracting or repelling of ions near the surface of the body or the movement of polar molecules near the surface of the body generate positive or negative charged surfaces which are believed to induce movement of ions and/or alignment of molecules within the wound or scar and it is further believed that this movement and/or alignment facilitates wound healing and/or scar reduction.

Figure 7:
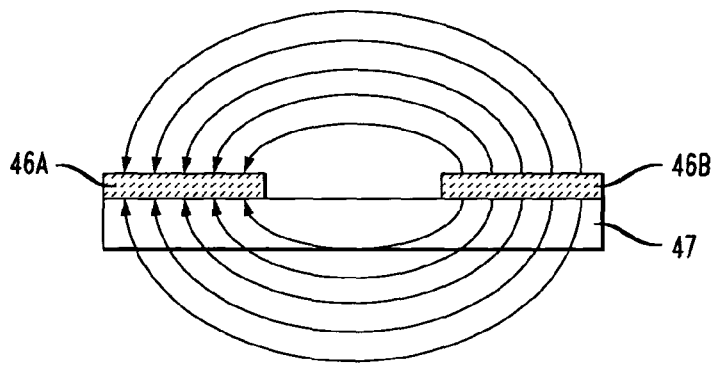
FIG. 7 is a diagrammatic view of a portion of the electrostatic field produced from the bandage of the present invention shown in FIG. 4.

Utilizing an applied voltage, a portion of the field lines for the embodiment of FIG. 3 are shown above and below the plates in FIG. 7. The field lines in the upper half are shown as they would appear through air. In the bottom half, the device is shown with a thin dielectric layer 47, exaggerated with respect to thickness for the sake of illustration. The field is modified somewhat by the presence of the dielectric layer, but a similar field exists external to the package. The term "thin" means that the dielectric layer is many times thinner than the width of the plate employed in the device.

In practice, a dielectric covers both sides of the plates. The size of the plates and the distance between them can be altered and the voltage can be varied to generate variations in the shape and intensity of the fields.

In addition to the dielectric material used as an insulating layer to prevent direct electrical contact with the wound or skin, other materials may be employed for this purpose. Without being bound by theory, it is believed that the inducement of a field under conditions controlling the intensity of the field as in the present invention can induce wound healing in a predetermined manner by modifying the field to specific regions of the wound. For example, the present invention can provide for greater intensity of the induced field at the center of the wound and lower intensity at the edges of the wound.

As previously indicated, the induced field is affected by the presence of a dielectric material. The effect on the induced field will depend on the particular dielectric material including the dielectric constant. A generated field external to the dielectric insulator will be produced by keeping the dielectric material as thin as practical. A good dielectric material will be highly insulative, to prevent excessive power requirements and to prevent direct electrical contact with the substrate (i.e. the skin). Suitable dielectrics include most plastics, silicones, etc. Particularly preferred dielectric materials are silicone based materials, polypropylene (e.g. having a dielectric constant of 1.3), polyethylene, polyesters gauze, materials such as those made out of cotton, and the like. It is important that the thickness of the dielectric material be small (e.g. 0.003 to 0.010 inch) compared to the width of the conductive material in order to maintain an induced field outside of the apparatus.

In one embodiment of the present invention, the spaced apart conductive materials are arranged in the form of a customized bandage to be applied to the patient. The conductive materials are in a pattern particularly suited for a particular wound or scar. Matched with the customized bandage is an apparatus for delivering a target induced field controlled with respect to intensity and optionally shape. The application of the present invention enables charged particles in the wound or scar to move into a new, desired orientation, and thus facilitate wound healing or scar reduction treatment.

The foregoing embodiments as described are exemplary of the invention and are not to be construed as to limiting the invention to only those embodiments.

What is claimed is:

1. A bandage for inducing a charge in a wound or scar of a warm blooded animal including humans to promote healing thereof comprising:
    an electrostatic field generating assembly for generating an electrostatic field and for directing the charge from the electrostatic field generating assembly toward said wound or scar comprising electrically conductive plates separated from each other by an insulative material of sufficient thickness to prevent electric current from passing between the plates, and a non-conductive outer insulative layer encasing said conductive plates to electrically isolate the body of the warm blooded animal from the electrically conductive plates, whereby no current passes into the wound or any other part of the warm-blooded animal's body;
    an electrical power source for supplying a current to the electrically conductive plates; and
    electrostatic field control means for controlling the intensity of the electrostatic field to achieve a wound or scar healing level of intensity sufficient to induce the charge in said wound or scar to promote healing.

2. The bandage of claim 1 wherein the control means comprises a signal generator including a voltage regulator, an amplifier and a current limiter for controlling the voltage delivered to the electrostatic field generating assembly.

3. The bandage of claim 2 wherein the control means comprises means for adjusting the voltage in a range of 0.1 mV to 2.0 kv.

4. The bandage of claim 2 wherein the signal generator comprises means for generating wave forms of varying frequency and polarity.

5. The bandage of claim 1 wherein the conductive plates are placed one over the other with the lower most plate being proximate to the wound or scar.

6. The bandage of claim 1, wherein the conductive plates are in the form of concentric circular rings.

7. The bandage of claim 1, wherein the conductive plates are in the form of concentric oval rings.

8. The bandage of claim 1 wherein the insulative material has a thickness in the range of from 0.003 to 0.010 inch.

9. The bandage of claim 1 wherein the insulative material is selected from the group consisting of silicone based materials, polypropylene, polyethylene, polyester, and cotton gauze.

10. The bandage of claim 9 wherein the insulative material is a silicone based material.

11. The bandage of claim 1 further comprising adhering means for adhering the bandage to the warm-blooded animal.

12. The bandage of claim 1, wherein the conductive plates are spaced apart, parallel and coplanar.

13. The bandage of claim 1 wherein the insulative material is a dielectric material.

14. The bandage of claim 1 wherein when the electrostatic field generated by the electrostatic generating assembly is applied, the wound or scar receives an induced charge opposite to that of at least one of the electrically conductive plate.

15. The bandage of claim 1 wherein the electrostatic field generating assembly is configured for inducing a change of polarity in said wound or scar.

16. The bandage of claim 1 wherein the electrostatic field generating assembly is configured for inducing a change of intensity in said wound or scar.

17. A method of treating wounds or scars in a warm-blooded animal including humans comprising applying a bandage capable of inducing a charge in said wound or scar to promote healing comprising:

an electrostatic field generating assembly for generating an electrostatic field and for directing the charge from the electrostatic field generating assembly toward said wound or scar, comprising electrically conductive plates separated from each other by an insulative material of sufficient thickness to prevent electric current from passing between the plates, and a non-conductive outer insulative layer encasing said conductive plates to electrically isolate the body of the warm blooded animal from the electrically conductive plates, whereby no current passes into the wound or any other part of the warm-blooded animal's body, an electric power source for supplying current to the electrically conductive plate, and electrostatic field control means for controlling the intensity of the electrostatic field, said method comprising:

applying a current to said electrostatic field generating assembly at a voltage sufficient to direct the charge toward said wound or scar and thereby inducing the charge therein at the site of the wound or scar at an intensity necessary to promote healing.

18. The method of claim 17 further comprising regulating the voltage applied to the electrostatic field generating assembly so that current does not pass into the wound or scar and a charge is produced on the insulative material sufficient to induce a charge of opposite polarity in the wound or scar.

19. The method of claim 18 further comprising regulating the wave function of the electrostatic field generating assembly so as to regulate the intensity, polarity or both intensity and polarity of the electrostatic field.

20. The method of claim 18 further comprising selecting an insulative material based on its insulative value and thickness for the electrostatic field generating assembly and selecting an operable voltage to generate a desired electrostatic field for a particular wound or scar.

21. The method of claim 20 further comprising selecting a current necessary to achieve said operable voltage.

22. The method of claim 18 wherein the insulative material is a dielectric material.

23. The method of claim 17 wherein the electrostatic field generating assembly is configured for inducing a change of polarity in said wound or scar.

24. The method of claim 17 wherein the electrostatic field generating assembly is configured for inducing a change of intensity in said wound or scar.

* * * * *